United States Patent
Zhang et al.

(10) Patent No.: US 10,080,649 B2
(45) Date of Patent: Sep. 25, 2018

(54) INTRAOCULAR DEVICES AND ASSOCIATED METHODS

(75) Inventors: Xioaxioa Zhang, Fort Worth, TX (US); Yin Yang, Arlington, TX (US)

(73) Assignee: Novartis AG, Basel (CH)

( * ) Notice: Subject to any disclaimer, the term of this patent is extended or adjusted under 35 U.S.C. 154(b) by 1199 days.

(21) Appl. No.: 12/960,653

(22) Filed: Dec. 6, 2010

(65) Prior Publication Data

US 2011/0153014 A1 Jun. 23, 2011

Related U.S. Application Data

(60) Provisional application No. 61/287,749, filed on Dec. 18, 2009.

(51) Int. Cl.
*A61F 2/16* (2006.01)

(52) U.S. Cl.
CPC .......... *A61F 2/1651* (2015.04); *A61F 2/1613* (2013.01); *A61F 2/1624* (2013.01); *A61F 2/1637* (2013.01); *A61F 2/1648* (2013.01); *A61F 2002/1699* (2015.04)

(58) Field of Classification Search
CPC ............ A61F 2/1624; A61F 2002/1699; A61F 2/1648; A61F 2/1613; A61F 2/1637; A61F 2/1651
USPC .... 623/6.23, 6.24, 6.27–6.29, 6.3, 6.32–6.34
See application file for complete search history.

(56) References Cited

U.S. PATENT DOCUMENTS

| | | |
|---|---|---|
| 4,666,446 A | 5/1987 | Koziol et al. |
| 4,769,033 A | 9/1988 | Nordan |
| 4,888,012 A | 12/1989 | Horn et al. |
| 4,932,971 A * | 6/1990 | Kelman ............... A61F 2/1648 623/6.34 |
| 5,217,489 A | 6/1993 | Van Noy et al. |
| 5,354,334 A | 10/1994 | Fedorov et al. |
| 5,354,335 A | 10/1994 | Lipshitz et al. |
| 5,391,202 A | 2/1995 | Lipshitz et al. |
| 5,476,514 A | 12/1995 | Cumming |
| 5,699,142 A | 12/1997 | Lee et al. |
| 5,814,103 A | 9/1998 | Lipshitz et al. |
| 5,876,442 A | 3/1999 | Lipshitz et al. |
| 5,895,422 A | 4/1999 | Hauber |
| 5,928,283 A | 7/1999 | Gross et al. |
| 5,941,886 A | 8/1999 | Feingold |
| 6,007,579 A | 12/1999 | Lipshitz et al. |
| 6,066,171 A | 5/2000 | Lipshitz et al. |

(Continued)

FOREIGN PATENT DOCUMENTS

WO 2006/023404 A3 3/2006

*Primary Examiner* — Howie Matthews

(57) ABSTRACT

Visual aids and associated methods for improving the eye sight of low vision patients are provided. Generally, the devices of the present disclosure address the needs of age-related macular degeneration (AMD) and other low vision patients by providing a magnified retinal image while keeping a large visual field of view. Further, the devices of the present disclosure allow direction of the magnified retinal image away from damaged portions of the retina and towards healthy, or at least healthier, portions of the retina. The devices of the present disclosure are also configured for implantation within the eye using minimally invasive surgical procedures. Methods of utilizing the devices of the present disclosure, including surgical procedures, are also provided.

22 Claims, 11 Drawing Sheets

(56) References Cited

U.S. PATENT DOCUMENTS

| | | |
|---|---|---|
| 6,197,057 B1 | 3/2001 | Peyman et al. |
| 6,416,550 B2 | 7/2002 | Freeman |
| 6,432,246 B1 | 8/2002 | Blake |
| 6,596,026 B1 | 7/2003 | Gross et al. |
| 6,599,317 B1 | 7/2003 | Weinschenk, III et al. |
| 6,638,305 B2 | 10/2003 | Laguette |
| 6,695,881 B2 | 2/2004 | Peng et al. |
| 6,902,577 B2 | 6/2005 | Lipshitz et al. |
| 6,969,403 B2 | 11/2005 | Peng et al. |
| 2002/0101564 A1 | 8/2002 | Herrick |
| 2002/0107568 A1 | 8/2002 | Zadno-Azizi et al. |
| 2003/0014107 A1 | 1/2003 | Reynard |
| 2004/0252274 A1 | 12/2004 | Morris et al. |
| 2005/0021138 A1 | 1/2005 | Woods |
| 2005/0209692 A1 | 9/2005 | Zhang |
| 2005/0267575 A1* | 12/2005 | Nguyen et al. .............. 623/6.34 |
| 2006/0055883 A1 | 3/2006 | Morris et al. |
| 2006/0100702 A1 | 5/2006 | Peyman |
| 2007/0270947 A1* | 11/2007 | Peyman ....................... 623/6.34 |
| 2000/0088841 | 4/2009 | Hong et al. |

\* cited by examiner

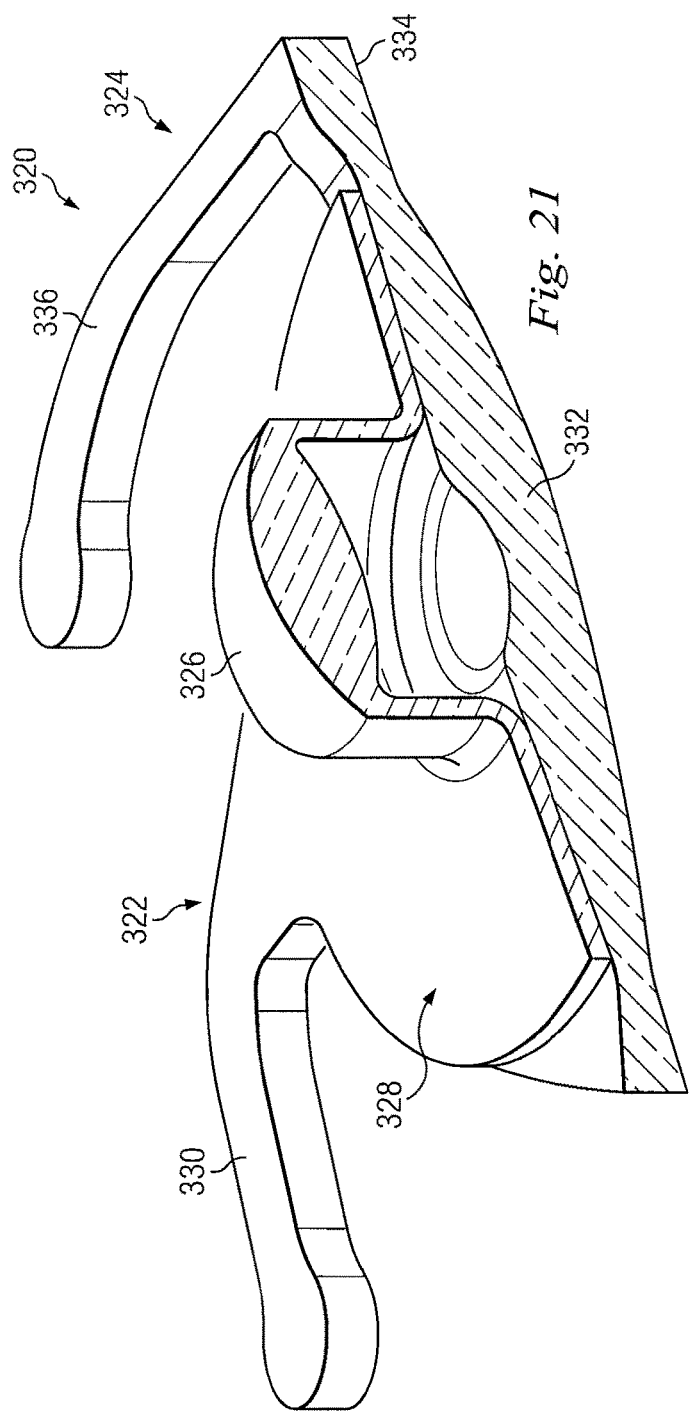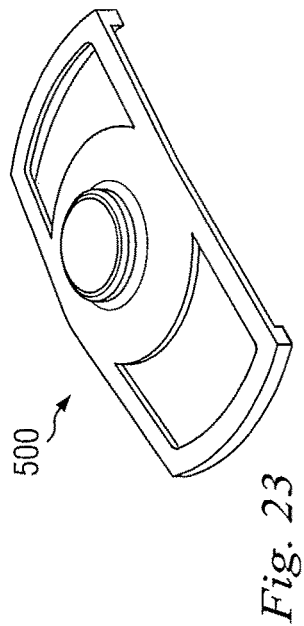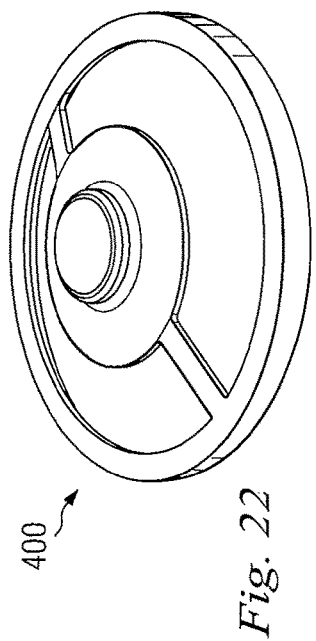
Fig. 21
Fig. 22
Fig. 23

INTRAOCULAR DEVICES AND ASSOCIATED METHODS

BACKGROUND OF THE INVENTION

This application claims the priority of U.S. Provisional Application No. 61/287,749 filed Dec. 18, 2009.

The present disclosure relates to a vision aid for patients with age-related macular degeneration (AMD) and other low vision conditions, including amblyopic patients. AMD patients usually have impaired central visual fields and often rely heavily on peripheral vision for daily tasks. Generally, the peripheral retina has low receptors densities relative to the central retina, which leads to a lower resolution ability. Low vision patients, such as those with AMD, also have poor central retina resolutions. In that regard, AMD patients often have compromised fovea. However, there are typically still functional retina receptors surrounding the compromised central receptors. These functional retina receptors are often peripherally located and have larger spacing between each other. The increased spacing results in a decreased image resolution. For example, at 3 degrees nasal retina, the visual acuity is reduced to 0.4 compared to the 1.0 visual acuity at 0 degrees, and at 5 degrees nasal retina, the visual acuity is reduced to 0.34 compared to the 1.0 visual acuity at 0 degrees.

Currently, there are three basic types of vision aids available for patients with low vision conditions. The first type is a single telescope. The single telescope is often mounted on the spectacles, which are heavy and are not appealing cosmetically. Implanted telescopes often require very large incisions during surgery to implant. The main disadvantages of using a telescope system are that the resultant visual field of view is narrowed and the overall image quality is poor. The narrow field of vision, or tunnel vision, creates a safety concern for the patient. In that regard, the narrow field of vision prevents the patient from recognizing movements that would normally be seen in the peripheral vision. Since the patient cannot see the peripheral movements, the patient will not react to those movements, which can potentially lead to patient injury.

The second type of vision aid is a prism. The prism is utilized to realign the line of sight to the peripheral retina. However, the prism must overcome a binocular fusion problem in order to avoid double imagery. Further, the prism does not magnify retinal images. So, the problem of low visual resolution caused by the larger peripheral retina receptor spacing cannot resolved with the prism.

The third type of vision aid is a magnifying glass. In some instances, the magnifying glass is combined with a prism. The magnifying glass is often used as a desk mount device, which limits the useful range of the device for patients. A handheld magnifying glass, while being portable, is not suitable for many elderly patients that have hand tremors because of the resulting vision instability and focus problems.

Therefore, there remains a need for improved vision aids for the low vision population, including patients with AMD.

SUMMARY OF THE INVENTION

The present disclosure provides visual aids and associated methods for low vision patients, including AMD patients.

In one embodiment, an intra-ocular lens system is provided. The intra-ocular lens system includes a first lens sized and shaped for implantation into a posterior chamber of an eye and a second lens sized and shaped for implantation into the posterior chamber of the eye and configured for engagement with the first lens. The first lens has a positive power optic with a first optical axis. The second lens has an anterior surface and an opposing posterior surface. A central portion of the second lens defines a negative surface power optic with a second optical axis, while a peripheral portion of the anterior surface defines a positive surface power optic. The first optical axis and the second optical axis are offset with respect to one another when the first and second lenses are engaged. In some instances, the first optical axis and the second optical axis extend substantially parallel to one another, but are offset by a distance between about 0.05 mm and about 0.75 mm. In some instances, the first optical axis and the second optical axis are offset by an oblique angle between about 1 degree and about 15 degrees.

In some instances, the central portion of the second lens defining the negative surface power optic includes a portion of the anterior surface. In some instances, the central portion of the second lens defining the negative surface power optic includes a portion of the posterior surface. In some instances, central portions of both the anterior and posterior surfaces define the negative surface power optic. In some instances, a peripheral portion of the posterior surface also has a positive surface power optic such that the peripheral portions of the anterior and posterior surfaces of the second lens form a single focal optic. In some instances, the power range of the single focal optic formed by the peripheral portions of the second lens is between 6 diopters and 34 diopters. In that regard, in some embodiments the positive power optic of the first lens has a first diameter and the second lens has a second diameter greater than the first diameter such that, when the first and second lenses are engaged, light passing around the positive power optic of the first lens passes through the single focal optic formed by the peripheral portions of the anterior and posterior surfaces of the second lens. The positive power optic of the first lens and the negative surface power optic of the anterior surface of the second lens provide an angular magnification between about 1.5× and about 4.0× in some configurations. In that regard, the positive power optic of the first lens and the negative surface power optic of the anterior surface of the second lens can produce a substantially collimated light beam within the second lens that is projected onto a central portion of the posterior surface of the second lens defining a positive surface power optic.

In some instances, the first lens includes a first haptic system and the second lens includes a second haptic system, where the first and second haptic systems are configured to produce the offset between the first optical axis and the second optical axis. In some configurations, the first and second lenses are configured for implantation into a capsular bag. In that regard, the first and second haptic systems may be configured such that at least a portion of the first lens protrudes through a capsular rhexis after the capsular bag is shrink-wrapped around the first and second haptic systems. The first and second haptic systems are configured in some embodiments such that the positive power optic of the first lens is spaced from the central portion of the anterior surface of the second lens by a distance between about 2.0 mm and about 4.0 mm when the first and second lenses are engaged. The first and second lenses are foldable to facilitate implantation of the lenses through an incision less than about 4.0 mm in length. In that regard, the first and second lenses are configured for insertion utilizing a cartridge system in some embodiments.

In another embodiment, an implantable apparatus that includes an anterior lens and a posterior lens is provided.

The anterior lens is sized and shaped for implantation into a posterior chamber of an eye. The anterior lens defining a positive power optic having a first optical axis such that, in combination with a cornea of the eye, the anterior lens provides a back focal length between about 3.0 mm and about 5.0 mm. The posterior lens is sized and shaped for implantation into the posterior chamber of the eye in a position posterior to the anterior lens. The posterior lens has an anterior surface and an opposing posterior surface. A central portion of the anterior surface defines a negative power optic surface having a second optical axis and a peripheral portion of the anterior surface defines a first positive power optic surface. A central portion of the posterior surface defines a second positive power optic surface and a peripheral portion of the posterior surface defines a third positive power optic surface. The first and third positive power optic surfaces of the peripheral portions of the anterior and posterior surfaces form a single focal optic with a power range between 6 diopters and 34 diopters. The anterior and posterior lenses include haptics configured to offset the first optical axis relative to the second optical axis by between about 0.05 mm and about 0.75 mm when the anterior and posterior lenses are implanted into the posterior chamber of the eye.

In some instances, the anterior and posterior lenses are configured for implantation into a capsular bag. In some instances, the haptics of the anterior and posterior lenses are configured such that at least a portion of the anterior lens protrudes through a capsular rhexis after the capsular bag is shrink-wrapped around the anterior and posterior lenses. Further, the haptics of the anterior and posterior lenses may be configured such that the anterior lens is spaced from the posterior lens by a distance between about 2.0 mm and about 4.0 mm when the anterior and posterior lenses are implanted into the posterior chamber of the eye. The anterior and posterior lenses are foldable to facilitate implantation through an incision less than about 4.0 mm in length, in some instances.

In another embodiment, a method for improving vision of a patient affected by age-related macular degeneration (AMD) and other vision problems is provided. The method includes implanting an intraocular lens system into a capsular bag such that a first optical axis of a first lens is offset with respect to a second optical axis of a second lens. The system is implanted such that the first lens and a central portion of the second lens project a magnified image onto an off-center portion of a retina and such that a peripheral portion of the second lens acts as a single focal optic with a power range between 6 diopters and 34 diopters and projects peripheral images onto the retina. In some instances, the method further includes identifying a damaged portion of the retina and orienting the first and second lenses within the capsular bag such that the offset of the first optical axis and the second optical axis directs the magnified image away from the damaged portion of the retina. In some embodiments, the offset of the first optical axis and the second optical axis directs the magnified image away from at least a portion of a fovea of the retina and towards a peripheral portion of the retina. The first and second lenses are inserted into the posterior chamber of the eye separately in some instances. In some embodiments, the first and second lenses are inserted into the posterior chamber of the eye utilizing a cartridge system. Further, in some embodiments the capsular bag is shrink-wrapped around the first and second lenses. In that regard, the first lens is implanted such that at least a portion of the first lens protrudes out of a capsular rhexis after the first and second lenses are shrink-wrapped by the capsular bag.

Generally, the devices of the present disclosure address the needs of AMD and other low vision patients by providing a magnified retinal image while keeping a large visual field of view. Further, the devices of the present disclosure allow direction of the magnified retinal image away from damaged portions of the retina and towards healthy, or at least healthier, portions of the retina. The devices of the present disclosure are also configured for implantation within the eye using minimally invasive surgical procedures. Other aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 21 is a cross-sectional perspective view of an intra-ocular lens system according to another aspect of the present disclosure.

FIG. 22 is a perspective top view of a lens for use in an intra-ocular lens system according to another aspect of the present disclosure.

FIG. 23 is a perspective top view of a lens for use in an intra-ocular lens system according to yet another aspect to the present disclosure.

DETAILED DESCRIPTION

Figure 1:
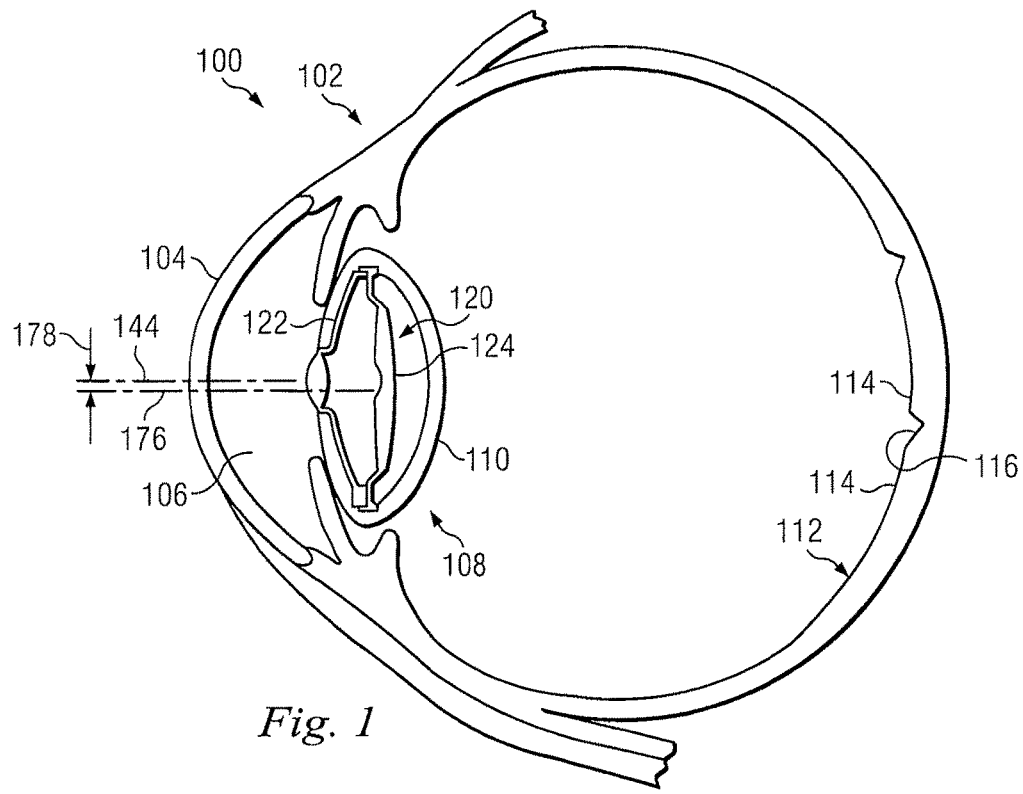
FIG. 1 is a diagrammatic cross-sectional side view of an eye with an implanted intra-ocular lens system according to one aspect of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Referring to FIG. 1, shown therein is an arrangement 100 illustrating aspects of the present disclosure. In that regard, FIG. 1 is a diagrammatic cross-sectional side view of an eye 102. The eye 102 includes a cornea 104, an anterior chamber 106, and a posterior chamber 108. A capsular bag 110 is illustrated in the posterior chamber 108. The eye 102 further includes a retina 112, including macula 114 and fovea 116. In general, the eye 102 represents the eye of an AMD or other low vision patient to which the present disclosure relates. An intra-ocular lens system 120 is implanted in the posterior chamber 108. In particular, the intra-ocular lens 120 is implanted within the capsular bag 110. As shown, the intra-ocular lens system 120 includes an anterior lens 122 and a posterior lens 124.

Figure 2:
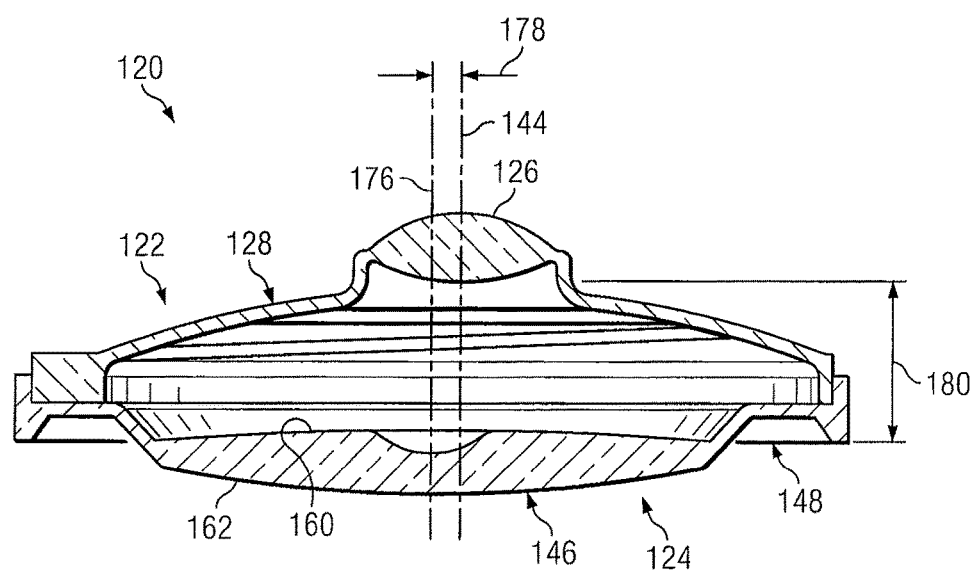
FIG. 2 is a cross-sectional side view of the intra-ocular lens system of FIG. 1.
Figure 3:
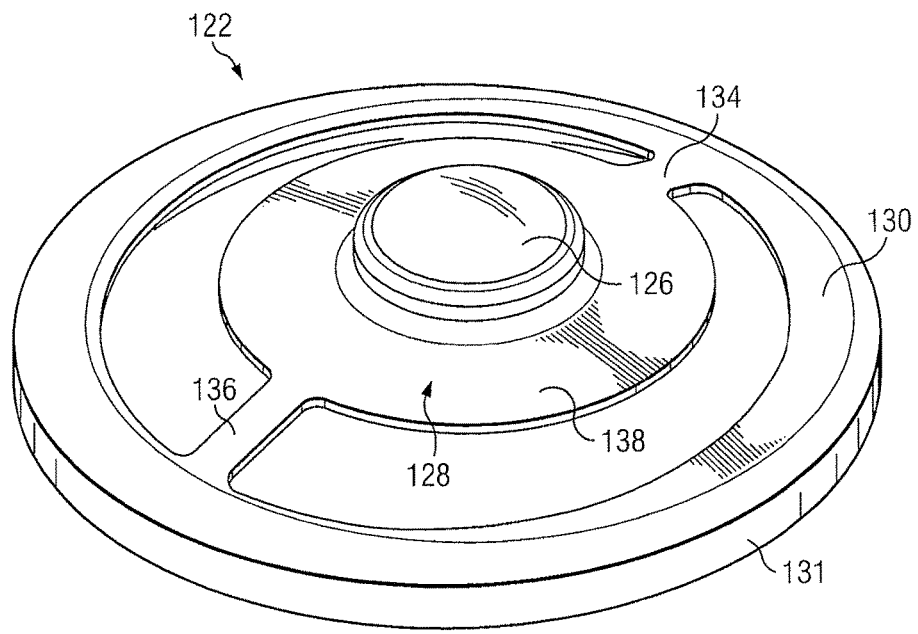
FIG. 3 is perspective top view of a lens of the intra-ocular lens system of FIGS. 1 and 2.
Figure 4:
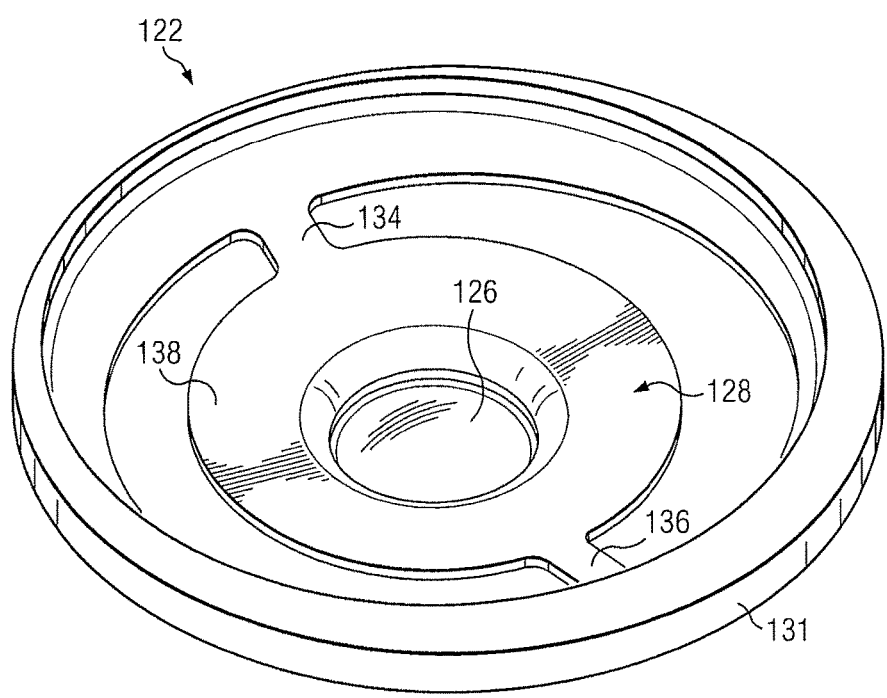
FIG. 4 is a perspective bottom view of the lens of FIG. 3.

Referring now to FIGS. 2, 3, 4, 5, 6, 7, 8, 9, 10, and 11, aspects of the intra-ocular lens system will be discussed in greater detail. In that regard, FIG. 2 is a cross-sectional side view of the anterior and posterior lenses 122, 124 of the intra-ocular lens system 120, FIGS. 3, 4, 5, and 6 are, respectively, perspective top, perspective bottom, top, and side views of the anterior lens 122, and FIGS. 7, 8, 9, 10, and 11 are, respectively, perspective top, perspective bottom, side, top, and bottom views of the posterior lens 124.

Referring more particularly to FIGS. 2, 3, 4, 5, and 6, the anterior lens 122 includes an optic 126. The optic 126 is a power positive optic. In the illustrated embodiment, the optic 126 is biconvex. That is, the anterior and posterior surfaces of the optic 126 are convex. In some embodiments, the optic 126 has a focal length between about 3.0 mm and about 7.0 mm and, in some instances, between about 5.0 mm and about 6.0 mm.

Figure 5:
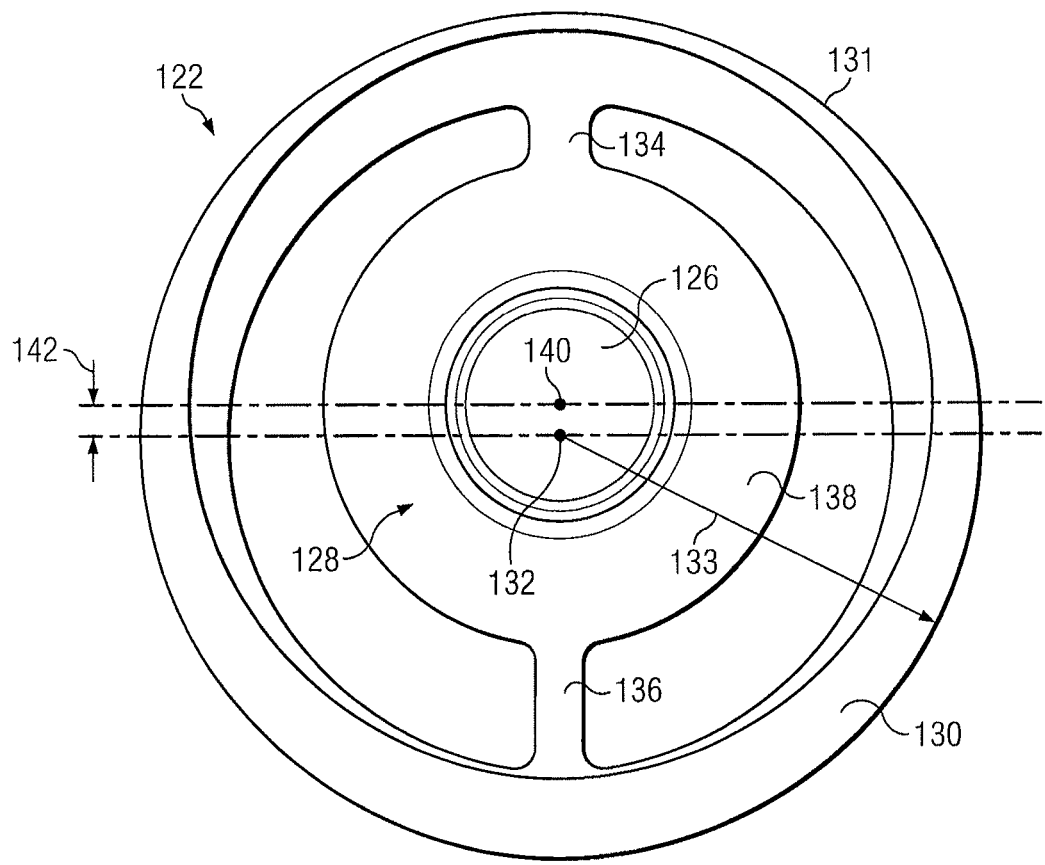
FIG. 5 is a top view of the lens of FIGS. 3 and 4.

The anterior lens 122 also includes haptics 128. As a general matter, the haptics 128 are configured to offset the optic 126 as will be discussed in greater detail below. In some instances, the haptics 128 are clear or translucent and provide substantially no optical power. In the illustrated embodiment, the haptics 128 have a rim 130 that defines an outer boundary 131. In the illustrated embodiment, the outer boundary 131 has a substantially circular profile centered about a center point 132, as best seen in FIG. 5. The outer boundary 131 is defined by a radius 133 extending from the center point. Generally, the radius 133 is between about 3.0 mm and about 5.5 mm and, in some instances, is between about 4.2 mm and about 4.8 mm.

Figure 6:
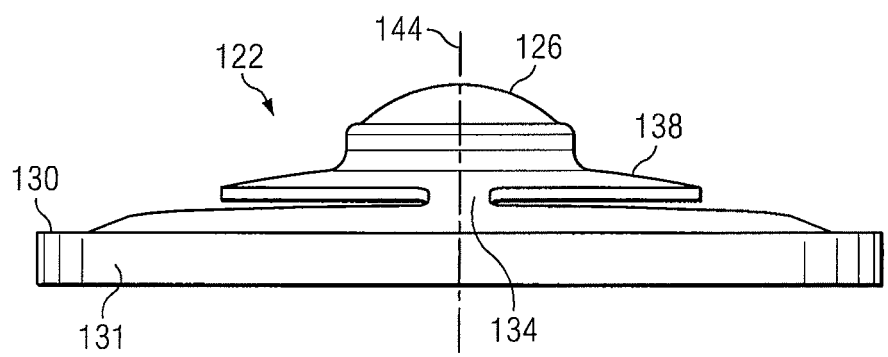
FIG. 6 is a side view of the lens of FIGS. 3, 4, and 5.

Extending inwardly from the rim 130 are arms 134 and 136. The arms 134, 136 connect the rim 130 to a mounting area 138. The mounting area 138 is configured to mount the optic 126 in a proper orientation. In that regard, the haptics 128 are configured to position the optic 126 such that it is offset relative to the center point 132. In particular, the optic 126 is centered about a center point 140 that is offset from the center point 132 by a distance 142. In some embodiments, the distance 142 is between about 0.05 mm and about 0.75 mm. As the optic 126 is centered about the center point 140, an optical axis 144 of the optic 126 extends through the center point 140, as shown in FIGS. 2 and 6. Referring again to FIG. 5, in the illustrated embodiment the mounting area 138 has a generally circular outer profile centered about the center point 140. Accordingly, mounting area 138 is offset relative to the center point 132. In that regard, the arms 134, 136 have different lengths to accommodate the offset position of the mounting area 138 and optic 126. In the illustrated embodiment, the arm 134 is shorter than the arm 136. While the two arms 134, 136 are illustrated, it is understood that any number of connections between the rim 130 and the mounting area 138 may be utilized.

Figure 9:
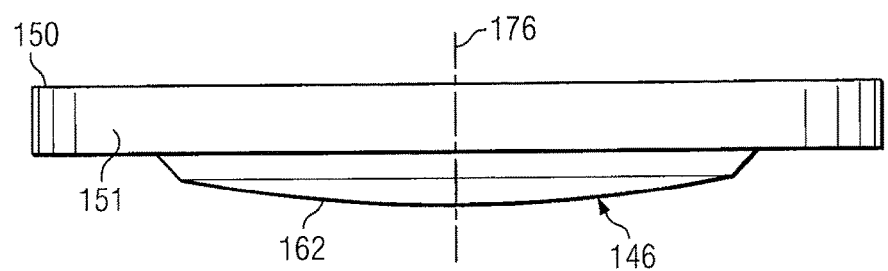
FIG. 9 is a side view of the lens of FIGS. 7 and 8.
Figure 10:
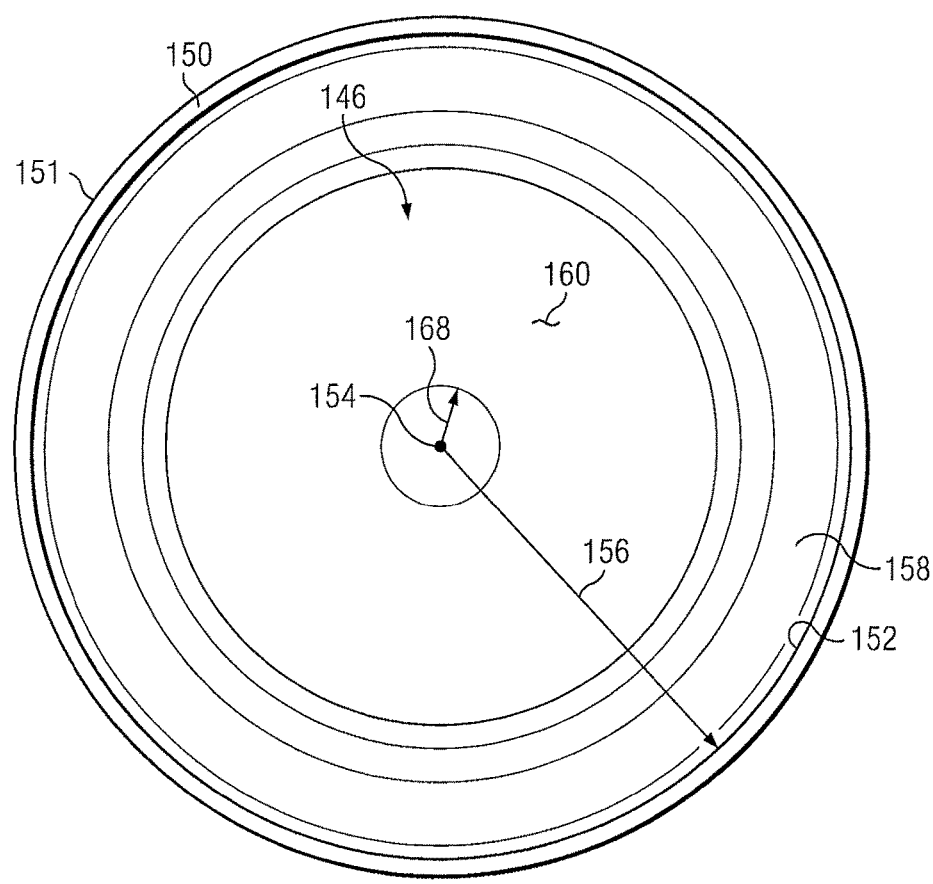
FIG. 10 is a top view of the lens of FIGS. 7, 8, and 9.

Referring more particularly to FIGS. 2, 7, 8, 9, 10, and 11, aspects of the posterior lens 124 will be discussed. As a general matter, the posterior lens 124 includes optics 146 and haptics 148. In the illustrated embodiment, the haptics 148 include a rim 150 that defines an outer boundary 151 and an inner boundary 152. In the illustrated embodiment, the outer boundary 151 and the inner boundary 152 have substantially circular profiles centered about a center point 154, as best seen in FIG. 10. As shown in FIG. 10, the inner boundary 152 is generally defined by a radius 156 extending from the center point 154. In that regard, the radius 156 is substantially equal to the radius 133 of the anterior lens 122 to allow mounting of the anterior lens 122 within the rim 150. The haptics 148 of the posterior lens 124 also include a surface 158 extending inwardly from the rim 150. In some instances, the surface 158 is configured to mate with a bottom surface of the rim 130 of the anterior lens 122. In that regard, the surface 158 is substantially planar in some embodiments. The surface 158 extends substantially perpendicular to the inner boundary 152 in the illustrated embodiment. In other instances, however, the surface 158 extends at an oblique angle relative to the inner boundary 152.

Figure 7:
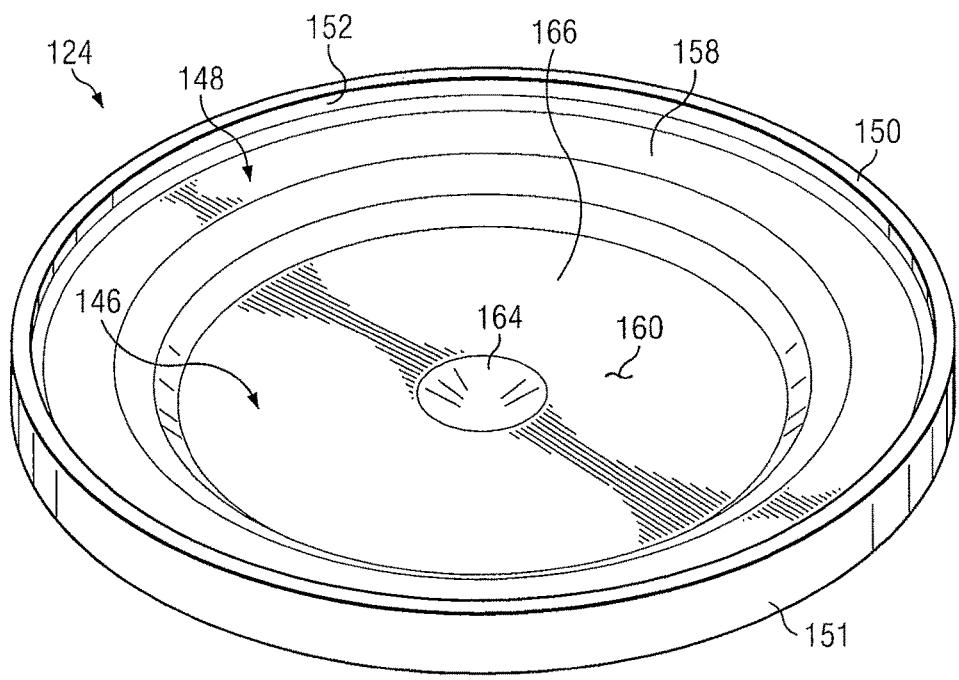
FIG. 7 is a perspective top view of another lens of the intra-ocular lens system of FIGS. 1 and 2.
Figure 8:
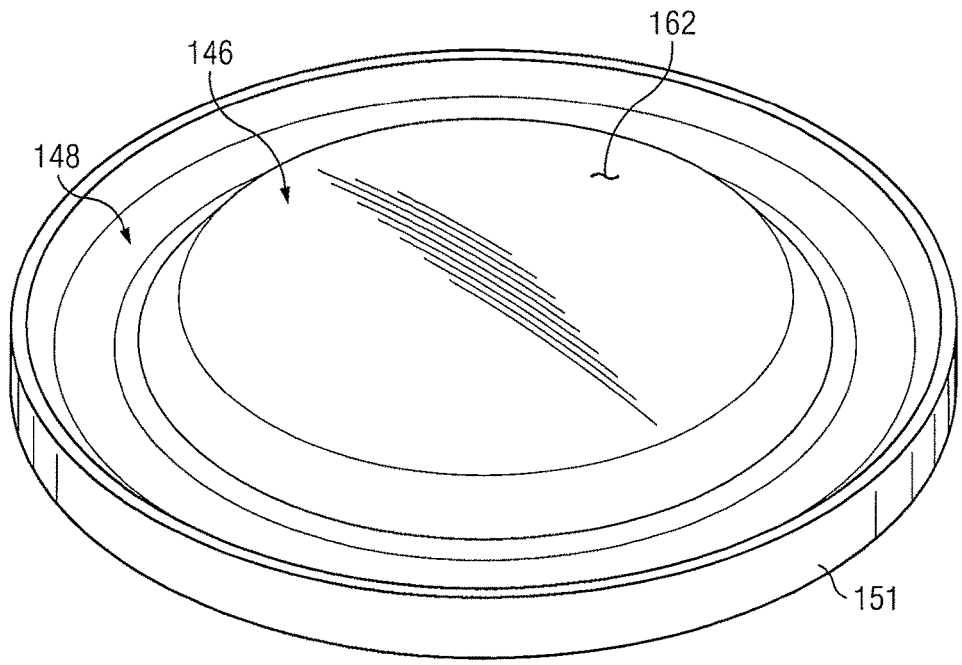
FIG. 8 is a perspective bottom view of the lens of FIG. 7.

As shown in FIG. 2, the optics 146 include an anterior surface 160 and a posterior surface 162. Referring to FIGS. 7 and 10, the anterior surface 160 includes a central portion 164 surrounded by a peripheral portion 166. In the illustrated embodiment, the central portion 164 has a generally circular profile defined by a radius 168 extending from the center point 154. In that regard, the radius 168 is generally between about 0.5 mm and about 4.0 mm. Relative to the anterior surface 160 as a whole, the central portion 164 is generally between about 10% and about 70% of the total surface area of the anterior surface 160. The central portion 164 defines a negative power surface optic. Accordingly, in the illustrated embodiment the central portion 164 of the anterior surface 160 is concave. The peripheral portion 166 defines a positive power surface optic. Accordingly, in the illustrated embodiment the peripheral portion 166 is convex. The transition between the central portion 164 and the peripheral portion 166 may be a smoothed or rounded transition, an abrupt transition (e.g., such that the transition defines an edge), and/or combinations thereof.

Figure 11:
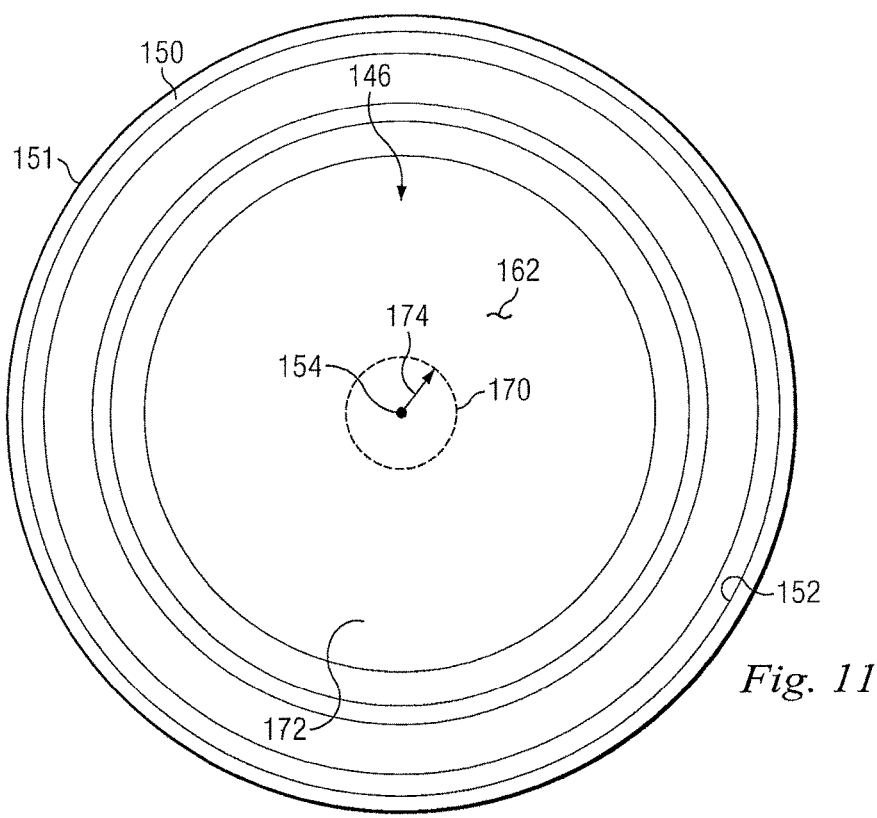
FIG. 11 is a bottom view of the lens of FIGS. 7, 8, 9, and 10.

Referring more particular to FIG. 11, the posterior surface 162 similarly includes a central portion 170 surrounded by a peripheral portion 172. In the illustrated embodiment, the central portion 170 has a generally circular profile defined by a radius 174 extending from the center point 154. In that regard, the radius 174 is generally between about 0.5 mm and about 4.0 mm. Relative to the posterior surface 162 as a whole, the central portion 170 is generally between about 10% and about 70% of the total surface area of the posterior surface 162. In some instances, the radius 174 defining the central portion 170 of the posterior surface 162 is substantially equal to the radius 168 defining the central portion 164 of the anterior surface 160. In other instances, the radius 174 is larger or smaller than the radius 168 such that the central portion 170 of the posterior surface 162 is correspondingly larger or smaller than the central portion 164 of the anterior surface 160.

The central portion 170 of the posterior surface 162 defines a positive power surface optic. Accordingly, in the illustrated embodiment the central portion 170 of the posterior surface 162 is convex. Similarly, the peripheral portion 172 of the posterior surface 162 also defines a positive power surface optic. Accordingly, in the illustrated embodiment the peripheral portion 172 is convex as well. The transition between the central portion 170 and the peripheral portion 172 may be a smoothed or rounded transition, an abrupt transition (e.g., such that the transition defines an edge), and/or combinations thereof. The central portion 170 is demarcated in phantom to illustrate the fact that the central portion 170 and the peripheral portion 172 are parts of a single continuous optical surface in some instances. In that regard, there is not a visible transition between the central portion 170 and the peripheral portion 172 in some instances. Further, in some instances, the central portion 170 and the peripheral portion 172 have the same positive optical power.

Generally, the central portion 164 of the anterior surface 160 and the central portion 170 of the posterior surface 162 project a magnified image towards the retina 112. As discussed below, in some instances the central portion 164 projects a substantially collimated beam of light towards the central portion 170, which then projects a resulting magnified image towards the retina 112. Further, in some embodiments the peripheral portions 166, 172 of the anterior and posterior surfaces 160, 162 together form a single focal optic. In that regard, the peripheral portions 166, 172 provide a power range between about 6 diopters and about 34 diopters in some instances. The particular strength of the single focal optic formed by the peripheral portions 166, 172 may be selected based on patient need. In that regard, the peripheral portions 166, 172 of the posterior lens 124 are utilized to project images of the peripheral field of vision onto the retina in some instances.

Generally, the optics 146 defined by the anterior surface 160 and the posterior surface 162 share a common optical axis 176, as shown in FIG. 9. The optical axis 176 generally extends through the center point 154 of the posterior lens 124. As shown in FIGS. 1 and 2, when the anterior lens 122 is engaged with the posterior lens 124, the optical axis 144 of the anterior lens is offset with respect to the optical axis 176 of the posterior lens by a distance 178. In that regard, engagement of the outer boundary 131 of the rim 130 of the anterior lens 122 with the interior boundary 152 of the rim 150 of the posterior lens 124 substantially aligns the center point 132 of the anterior lens with the center point 154 of the posterior lens. Accordingly, the optic 126 of the anterior lens 122 is offset with respect to the optics 146 of the posterior lens by a distance equal to the offset distance of the optic 126 relative to the center point 132. Since the optical axis 176 of the posterior lens extends from the center point 154, the offset distance 178 between the optical axes 144, 176 is substantially equal to the offset distance 142. Accordingly, in some instances the offset distance 178 is between about 0.05 mm and about 0.75 mm. As shown in FIG. 2, when the anterior lens 122 is engaged with the posterior lens 124, the optic 126 of the anterior lens is spaced from the optics 146 of the posterior lens by a distance 180. In that regard, the distance 180 represents the distance between the posterior-most portion of the optic 126 and the anterior-most portion of the optics 146. In some instances, the distance 180 is between about 2.0 mm and about 4.0 mm, but may be outside of this range in some instances. In some instances, the distance 180 is determined based on the focal length of the optic 126. In that regard, the distance 180 may be selected such that the focal point of the optic 126 falls within the optics 146 of the posterior lens 124.

Figure 12:
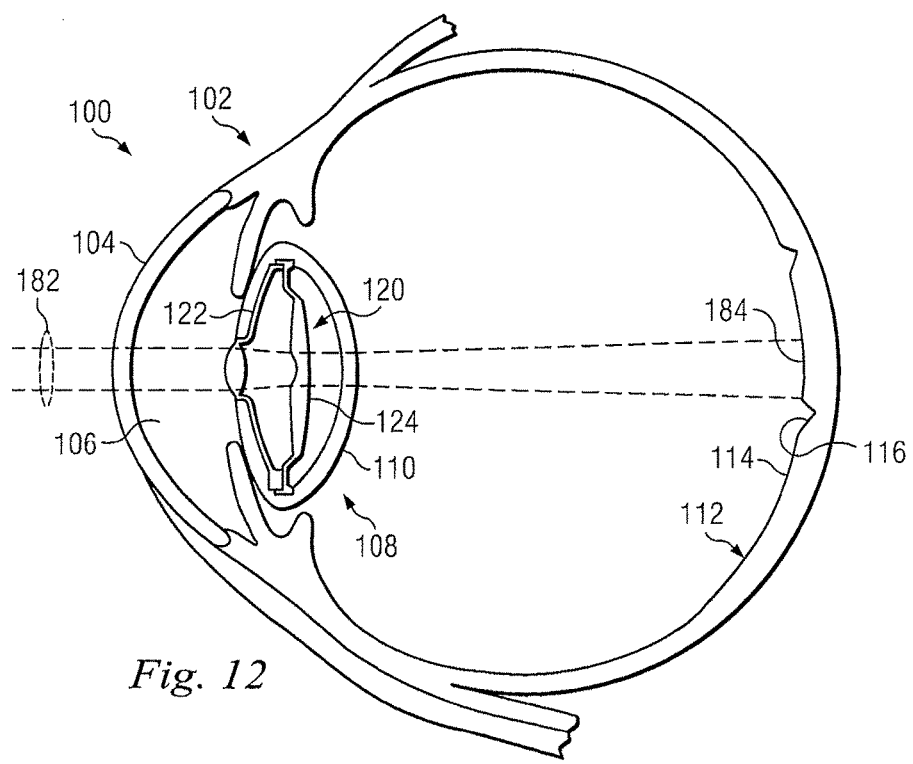
FIG. 12 is a diagrammatic cross-sectional side view of the eye with the implanted intra-ocular lens system of FIG. 1 illustrating the projection of a magnified retinal image to an off-center location of the retina according to one aspect of the present disclosure.

Referring now to FIG. 12, the offset between the optic 126 of the anterior lens 122 and the optics 148, in particular the central portions 164, 170, of the posterior lens 124 results in an a corresponding offset in the image projected onto the retina 112. In particular, light 182 representing a central field of vision comes into the eye 102 and passes through the cornea 104 and into optic 126 of the anterior lens 122. The optic 126 focuses the light 182 towards the central portion 164 of the anterior surface 160 of the posterior lens. In some instances, the cornea 104, optic 126, and central portion 164 form an afocal Galilean telescope having an angular magnification in the range of 1.5× to 4.0×. In that regard, the cornea, optic 126, and central portion 164 produce a substantially collimated light beam within the posterior lens 124 that is directed towards the central portion 170 of the posterior surface 162, in some embodiments. The light passes through the central portion 170 of the posterior surface 162 and is projected onto the retina 112. In that regard, offset distance 178 between the optical axes 144 and 176 determines the amount of offset of the resulting magnified image 184 relative to a center point of the fovea. In general, the greater the offset distance 178, the greater the amount of offset of the resulting magnified image 184. In that regard, it is contemplated that a surgical kit for the intra-ocular lens system 120 may include a plurality of anterior lenses 122 having different offsets such that an anterior lens with the appropriate amount of offset for a particular patient may be selected.

Further, in addition to the amount of offset of the resulting image 184, the direction of the offset may also be selected. In that regard, in some instances the anterior lens 122 is oriented relative to the posterior lens 124 such that the magnified image 184 produced by the intra-ocular lens system 120 is directed away from a damaged portion of the macular 114, such as all or a portion of the fovea 116, and towards a healthier portion of the retina 112. In that regard, the anterior lens 122 may be rotated relative to the posterior lens 124 to adjust the direction of the offset. The anterior lens 122 may be rotated 360 degrees relative to the posterior lens 124 such that the magnified image 184 may be directed up, down, left, right, and/or combinations thereof. In the illustrated embodiment, the circular profiles of the rims 130 and 150 result in the amount of offset being substantially constant. However, by providing a plurality of anterior lenses with different amounts of offset, as discussed above, and the fact that the direction of offset is selectable via rotation of the anterior lens relative to the posterior lens, the direction and magnitude of the offset can generally be tailored to fit the needs of any AMD or other low vision patient.

To facilitate proper orientation of the lenses 122, 124 and, in particular, the optic 126 of the anterior lens 122, one or both of the lenses 122, 124 may include markings, an index, and/or other feature(s) to indicate a relative position of the lenses. In that regard, the markings, index, and/or other feature(s) can signify to a surgeon the direction of offset of the optic 126 and, thereby, the direction in which the resulting magnified image 184 of the intra-ocular system will be directed relative to a center point of the fovea. Accordingly, if, for example, the patient has damage in a lower left quadrant of the fovea, the lenses 122, 124 can be oriented to direct the magnified image 184 towards the upper right quadrant of the fovea and surrounding portions of the macular and retina. In some instances, the markings, index, and/or other feature(s) are part of the rim 130 of the anterior lens 122. In some instances, the structure of the haptics 128 of the anterior lens 122 is utilized to identify to the surgeon or caregiver the direction of offset of the optic 126. Identifying the portions of the fovea, macular, and/or retina that are damaged and, therefore, the appropriate direction for offsetting the magnified image 184 may be determined utilizing standard techniques (e.g., retinal scope) prior to implantation of the intra-ocular lens system 120. In that regard, a calculator program can propose a suggested position for the magnified image 184 and provide the corresponding orientation of the lenses 122, 124 based on data received from pre-implantation testing. Alternatively, the intra-ocular lens system 120 may be implanted and then tuned or adjusted to provide the best vision for the patient. In that regard, the orientation of the lenses 122, 124 may be adjusted after implantation to accommodate for future changes in the patient's eyesight. For example, if the area initially selected to receive the magnified image 184 itself becomes damaged, then the another suitable area can be identified and the orientation of the lenses 122, 124 adjusted to direct the magnified image there. In this manner, the intra-ocular lens system 120 may be tailored to a patient's needs even long after initial implantation.

The magnified image 184 discussed above is generally produced by the optic 126 of the anterior lens 122 and the central portions 164, 170 of the posterior lens 124. In that regard, the magnified image 184 is of a central field of vision and, importantly, the resulting magnified image 184 does not occupy the entire field of vision of the patient. Rather, magnified image 184 is projected only over a portion of the retina 112 such that images from the peripheral field of vision are also projected onto the retina. In that regard, light passing into the eye representing the peripheral field of vision misses the optic 126 of the anterior lens 122 and passes through to the peripheral portions 166, 172 of the posterior lens. As discussed above, the peripheral portions 166, 172 together form a single focal optic that is utilized to project the light representative of the peripheral field of vision onto the retina. In that regard, the peripheral portions 166, 172 provide a power range between about 6 diopters and about 34 diopters in some instances. The particular strength of the single focal optic formed by the peripheral portions 166, 172 may be selected based on patient need. Accordingly, the intra-ocular lens system 120 provides the patient with both an improved magnified image 184 of the central field of vision without causing tunnel vision by still providing the peripheral field of vision to the surrounding portions of the retina.

In some instances, the deflection of the magnified image 184 is utilized to avoid scotoma in the visual field. For example, deflection of the image 184 is particularly useful for AMD patients who have undergone macular translocation surgeries. In that regard, macular translocation is a surgical technique designed to move the area of the retina responsible for fine vision (macula) away from the diseased underlying layers (the retinal pigment epithelium and choroid). Generally, the macula is moved to an area where these underlying tissues are healthier. For patients who have undergone macular translocation surgeries, their normal line of sight is no longer aligned with their macula. Consequently, the macular translocation treated eye could show the undesirable "tropia" appearances, such as "esotropia" or "exotropia". Further, in cases where the patient has both eyes treated with macular translocation surgeries, there can be negative impact to the intended vision function. For example, if the left eye needs to look up to see better and the right eye needs to look down to see better, then the patient will have a difficult time seeing clearly with both eyes because such binocular eye movements are very difficult to perform. Redirecting the retinal image location can reduce or correct the "tropia" appearances by relocating the line of sight to the new macular location. Further, the intra-ocular lens systems of the present disclosure allow redirecting the retinal image location for each eye, such that in the case of dual macular translocation the need for binocular eye movements is eliminated or greatly reduced.

The lenses 122, 124 of the intra-ocular lens system 120 are configured for implantation into the capsular bag 110 in the posterior chamber 108 of the eye 102 utilizing minimally invasive techniques. Accordingly, the intra-ocular lens system avoids the complications associated with a combination anterior chamber and posterior chamber system, while still providing the benefits of minimally invasive surgical techniques. In that regard, the lenses 122, 124 are configured for implantation through an incision or capsular rhexis having a length less than about 4.0 mm and, typically, less than 3.5 mm. In some instances, the lenses 122, 124 are configured for implantation utilizing a cartridge system, including cartridge systems commercially available from Alcon. In some instances, the lenses 122, 124 are engaged with one another prior to implantation. In other instances, the lenses 122, 124 are inserted into the capsular bag 110 separately. For example, in some embodiments, the posterior lens 124 is inserted into the capsular bag 110. Then the anterior lens 122 is inserted into the capsular bag 110 and engaged with the posterior lens 124. In some instances, the capsular bag 110 is shrink-wrapped around the lenses 122, 124 after implantation to securely engage the lenses. Further, in some embodiments at least a portion of the optic 126 of the anterior lens 122 is sized and shaped to extend through the incision or capsular rhexis in the capsular bag 110 after the capsular bag has been shrink-wrapped around the lenses. Further, in some embodiments, the size and shape of the lenses 122, 124 helps prevent interlenticular cell growth. In that regard, the structure of at least the anterior lens facilitates easier contact between the anterior capsular leaflets and the posterior capsule. In some instances, the diameter of the optic 126 being smaller than the capsular rhexis opening combined with the central leg spacing of the haptics results in easier contact with the anterior capsular leaflets, thereby limiting or preventing unwanted interlenticular cell growth. In some instances, shrink-wrapping of the capsular bag 110 around the lenses 122, 124 seals off the circumferential space around the optics of the lenses to prevent interlenticular cell growth.

Figure 13:
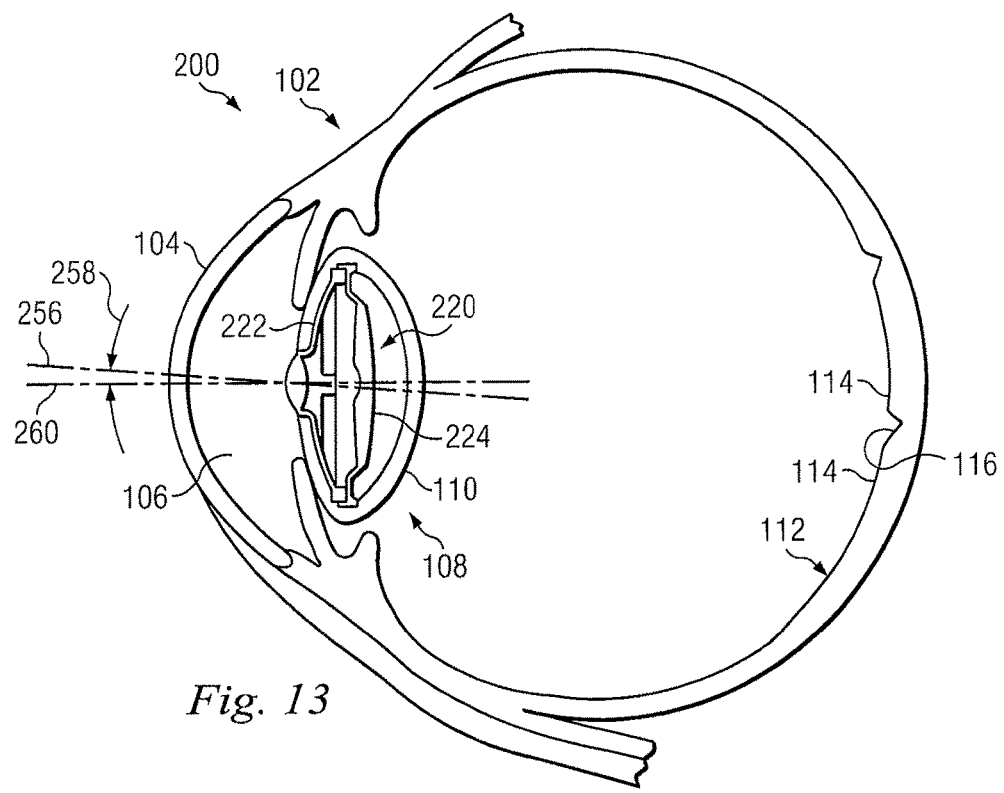
FIG. 13 is a diagrammatic cross-sectional side view of an eye with an implanted intra-ocular lens system according to another aspect of the present disclosure.

Referring to FIG. 13, shown therein is an arrangement 200 illustrating an alternative embodiment of the present disclosure. Specifically, an intra-ocular lens system 220 is implanted within the capsular bag 110 in the posterior chamber 108 of the eye 102. As shown, the intra-ocular lens system 220 includes an anterior lens 222 and a posterior lens 224. As a general matter, the intra-ocular lens system 220 provides functionality similar to that of intra-ocular lens system 120 described above. For example, the intra-ocular lens system 220 provides a magnified retinal image that is directed away from a damaged portion of the macular 114, such as all or a portion of the fovea 116, while still providing peripheral images to the retina. However, instead of the having optical axis of the anterior lens 222 offset relative to the optical axis of the posterior lens 224 by a particular distance (with the optical axes extending substantially parallel to one another), the optical axis of the anterior lens is at an oblique angle relative to the optical axis of the posterior lens in the intra-ocular lens system 220.

Figure 14:
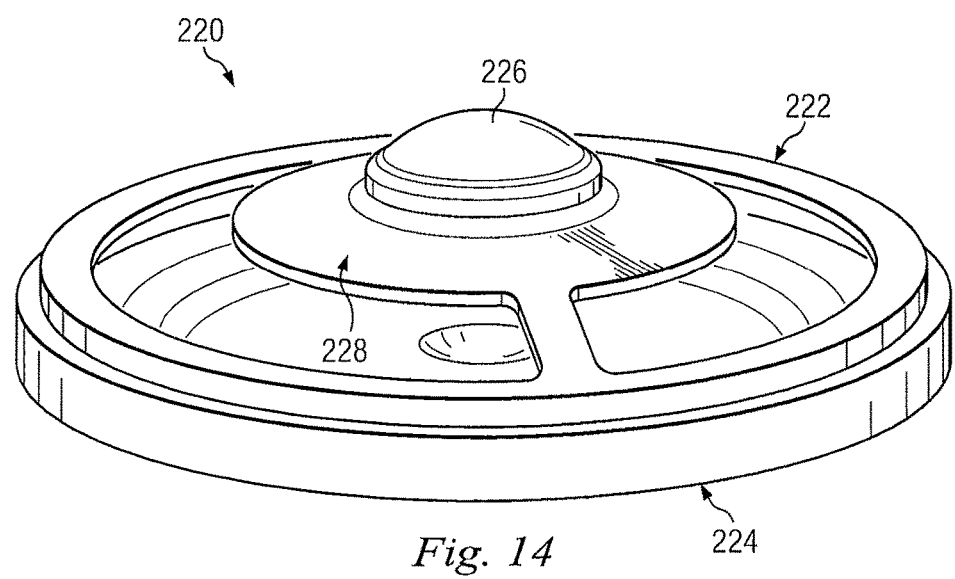
FIG. 14 is a perspective top view of the intra-ocular lens system of FIG. 13.
Figure 15:
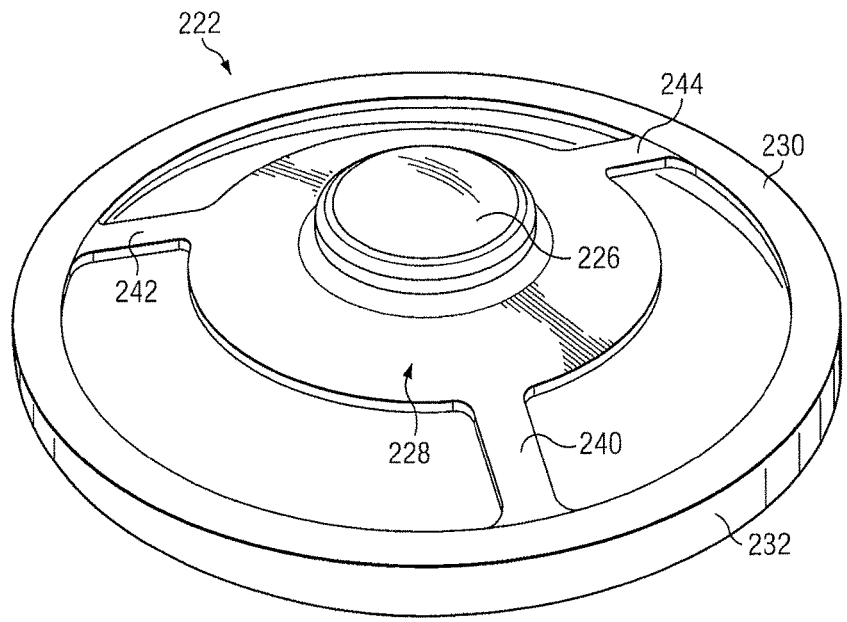
FIG. 15 is a perspective top view of a lens of the intra-ocular lens system of FIGS. 13 and 14.
Figure 16:
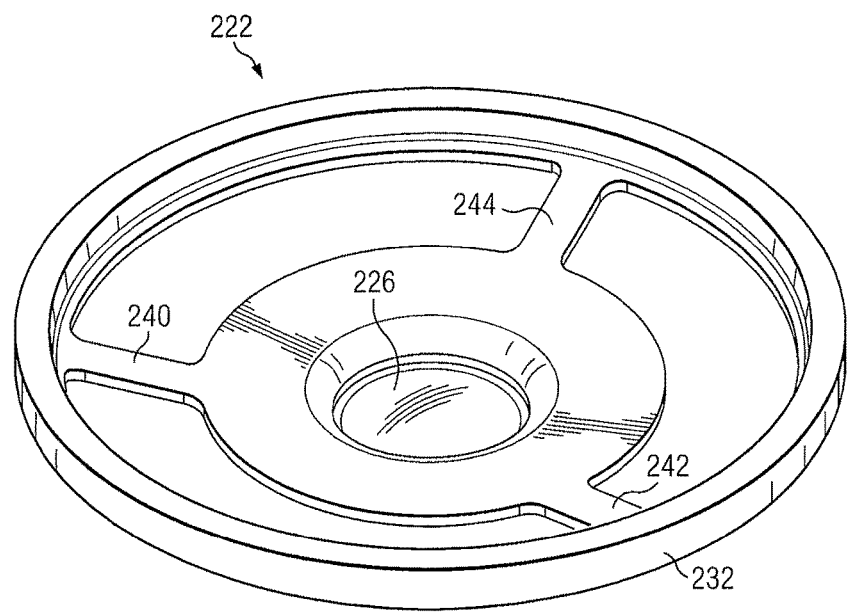
FIG. 16 is a perspective bottom view of the lens of FIG. 15.

Referring now to FIGS. 14, 15, 16, 17, 18, and 19, aspects of the intra-ocular lens system 220 will be discussed in greater detail. In that regard, in the illustrated embodiment the posterior lens 224 is substantially similar to the posterior lens 124 discussed above and, therefore, will not be discussed in detail here. Accordingly, the current focus will be on the features of the anterior lens 224. In that regard, FIG. 14 is a perspective top view of the anterior and posterior lenses 222, 224 of the intra-ocular lens system 220, while FIGS. 15, 16, 17, 18, and 19 are, respectively, perspective top, perspective bottom, side, front, and top views of the anterior lens 222.

As shown, the anterior lens 222 includes an optic 226. The optic 226 is a power positive optic. In the illustrated embodiment, the optic 226 is biconvex. That is, the anterior and posterior surfaces of the optic 226 are convex. In some embodiments, the optic 226 has a focal length between about 3.0 mm and about 7.0 mm and, in some instances, the focal length is between about 5.0 mm and about 6.0 mm.

Figure 19:
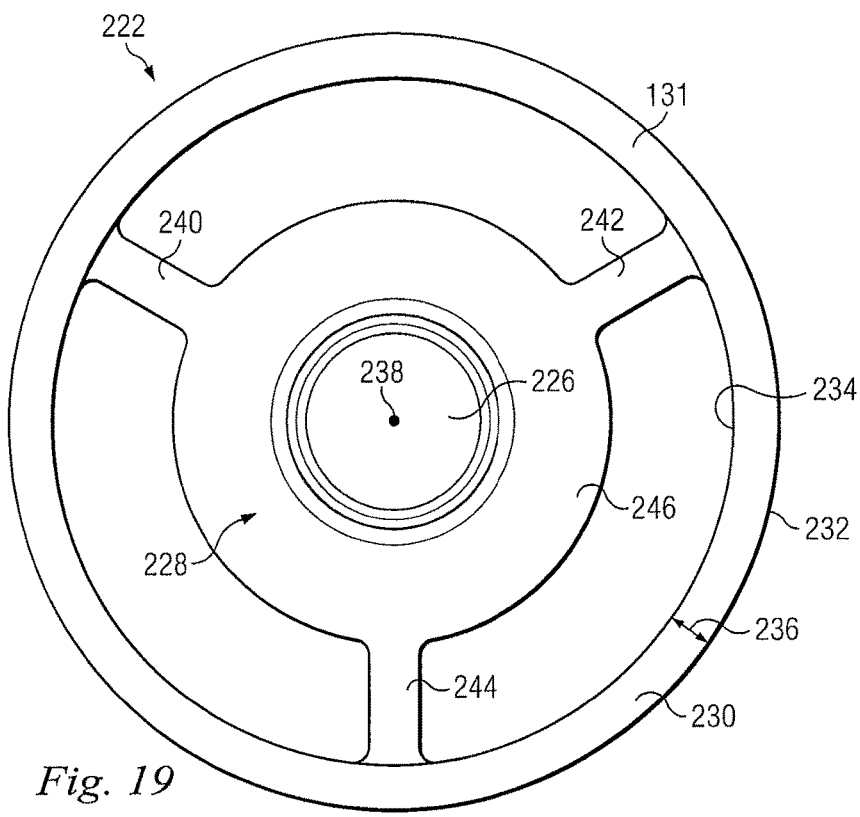
FIG. 19 is a top view of the lens of FIGS. 15, 16, 17, and 18.

The anterior lens 222 also includes haptics 228. As a general matter, the haptics 228 are configured to angularly offset the optic 226, as will be discussed in greater detail below. In some instances, the haptics 228 are clear or translucent and provide substantially no optical power. In the illustrated embodiment, the haptics 228 have a rim 230 that defines an outer boundary 232 and an inner boundary 234. In the illustrated embodiment, the rim 230 has a substantially constant thickness 236 between the outer boundary 232 and the inner boundary 234. In that regard, the outer boundary 232 and the inner boundary 234 have a substantially circular profiles centered about a center point 238, as best seen in FIG. 19. In some instances, the outer boundary has a radius between about 3.0 mm and about 5.5 mm and, in some instances, is between about 4.2 mm and about 4.8 mm. However, in other embodiments, the rim 230 has other profiles. For example, FIG. 21 illustrates an embodiment of an anterior lens 400 according to another aspect of the present disclosure. In that regard, the lens 400 is similar to anterior lens 222, except that portions of opposing sides of the lens have been removed such that the outer boundary of the lens defines a generally rectangular profile with rounded ends. In some embodiments, the rounded end portions have a partially circular profile, similar that of rim 230, such that the lens 400 can interface with a posterior lens (such as lenses 124 and 224) in a similar manner.

Extending inwardly from the rim 230 are arms 240, 242, and 244. The arms 240, 242, 244 connect the rim 230 to a mounting area 246. In the illustrated embodiment, the arms 240, 242, 244 have substantially equal lengths. While the three arms 240, 242, and 244 are illustrated, it is understood that any number of connections between the rim 230 and the mounting area 246 may be utilized. For example, FIG. 22 shows an embodiment of an anterior lens 500 according to another aspect of the present disclosure. In that regard, the lens 500 is substantially similar to lens 222, except that the lens 500 only has two arms connecting the rim to the mounting area where the optics are positioned. Referring again to, FIG. 19, the mounting area 246 is configured to mount the optic 226 in a proper orientation. In that regard, the haptics 228, including mounting area 246, are configured to position the optic 126 such that it will be angular offset relative to the optics of the posterior lens when the anterior and posterior lenses are engaged with one another.

Figure 17:
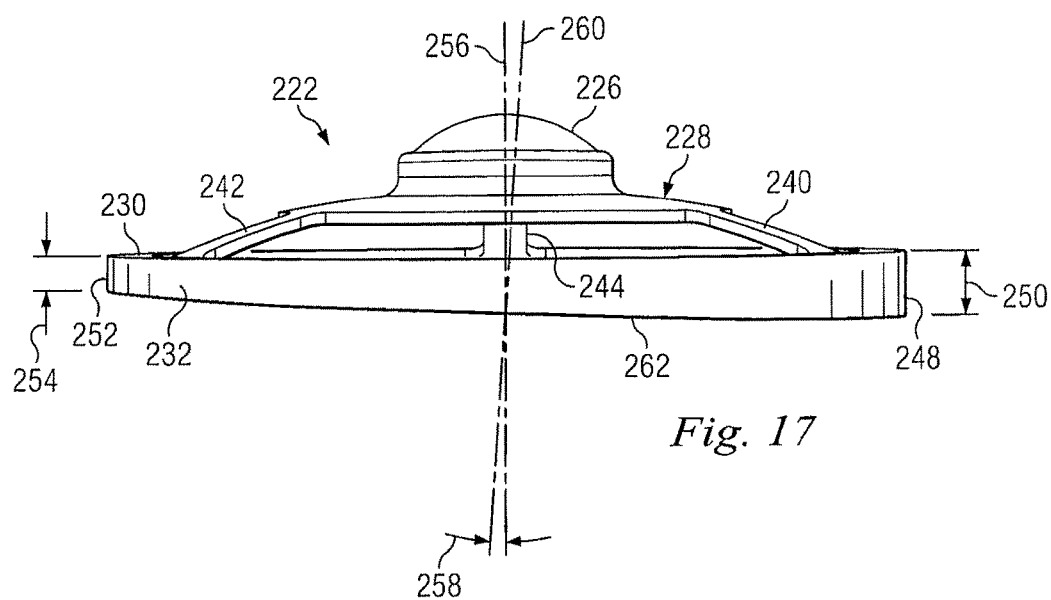
FIG. 17 is a side view of the lens of FIGS. 15 and 16.
Figure 18:
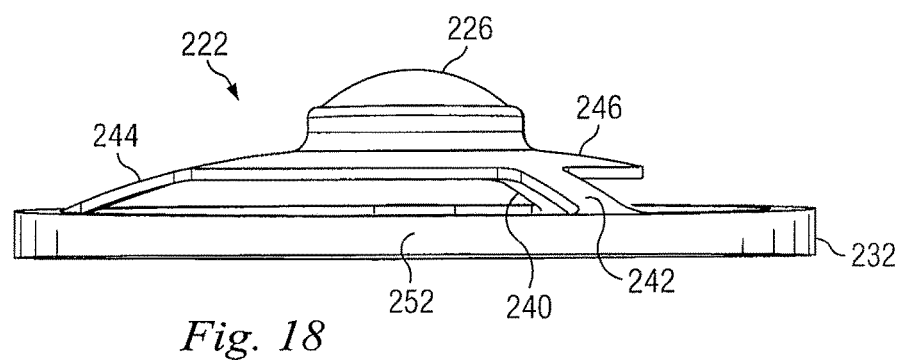
FIG. 18 is a front view of the lens of FIGS. 15, 16, and 17.

As best seen in FIG. 17, in the illustrated embodiment, the haptics 228 of the anterior lens 222 define an end 248 of the rim 230 having a height or thickness 250 and an opposing end 252 having a height or thickness 254. In that regard, the height 250 is greater than the height 254 such that the rim 230 tapers between the end 248 and the end 252. As shown, the rim 230 has a continuous and constant taper between the ends 248, 252 in the illustrated embodiment. As the arms 240, 242, 244 are spaced about the circumference of the rim 230 and are substantially equal in length, the mounting area 246 is angled by an amount matching the taper of the rim 230. Accordingly, the amount of angle of the mounting area 246 can be adjusted by changing the relative heights between the ends 248 and 252. In the illustrated embodiment, the optic 226 is mounted on the mounting area 246 such that it is also angled to match the taper of the rim 230. In that regard, the optic 226 defines an optical axis 256 that extends at an oblique angle 258 relative to an axis 260 extending substantially perpendicular to a lower surface 262 of the anterior lens 222, as best seen in FIGS. 13 and 17. In that regard, the lower surface 262 is a generally planar surface configured to mate with a surface of the posterior lens 224 similar to surface 158 of posterior lens 124 discussed above. Generally, the oblique angle 258 is between about 0.5 degrees and about 15 degrees, but may be outside of this range in some instances.

In some instances, the axis 260 is substantially aligned with an optical axis of the optics of the posterior lens 224 when the anterior lens 222 and the posterior lens are engaged. In other instances, the axis 260 and the optical axis of the optics of the posterior lens 224 extend substantially parallel to one another, but are separated by a distance between about 0.05 mm and about 1.5 mm. In such embodiments, the optical axis 256 of the optic 226 is offset with respect to the optical axis of the optics of the posterior lens in both angular and distance orientations. Generally, the particular angular and/or distance offset between the optical axes of the anterior and posterior lenses 222, 224 is selected in order to project a magnified image to a desired portion of the retina 112.

Figure 20:
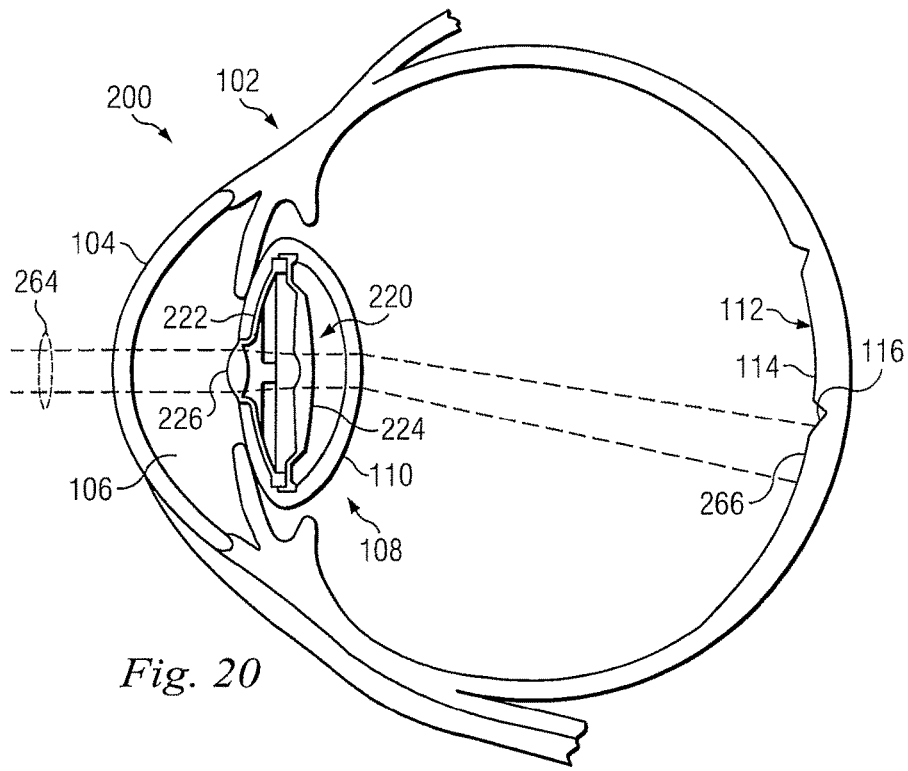
FIG. 20 is a diagrammatic cross-sectional side view of the eye with the implanted intra-ocular lens system of FIG. 13 illustrating the projection of a magnified retinal image to an off-center location of the retina according to one aspect of the present disclosure.

Referring now to FIG. 20, the angular offset of the optic 226 of the anterior lens 222 relative to an optical axis of the optics of the posterior lens 124 results in an a corresponding offset in the image projected onto the retina 112. In particular, light 264 representing a central field of vision comes into the eye 102 and passes through the cornea 104 and into optic 226 of the anterior lens 222. The optic 226 focuses the light 264 towards the posterior lens 224, which projects a magnified image 266 onto the retina 112. In that regard, angle 258 of the offset between the optical axis 256 of the optic 226 and the optical axis of the posterior lens 224 determines the amount of offset of the resulting magnified image 266 relative to a center point of the fovea. In general, the greater angle 258, the greater the amount of offset of the resulting magnified image 266, assuming the anterior lens 222 is centered about the posterior lens 224 such that the optical axis of the posterior lens 224 substantially coincides with the axis 260. It is contemplated that a surgical kit for the intra-ocular lens system 220 may include a plurality of anterior lenses 222 having different angular offsets such that an anterior lens with the appropriate amount of offset for a particular patient may be selected. Generally, the lenses 222, 224 may be manipulated in a similar manner to lenses 122 and 124, discussed above, in order to adjust the position of the magnified image 266 on the retina.

Referring now to FIG. 21, shown therein is perspective cross-sectional view of an intra-ocular lens system 320 according to another embodiment of the present disclosure. In that regard, the intra-ocular lens system 320 includes an anterior lens 322 and a posterior lens 324. The anterior lens 322 includes a power positive optic 326 similar to optics 126 and 226 above. The anterior lens 322 further includes haptics 328. The haptics 328 include an arm 330, as shown. It is understood that the anterior lens 322 includes another arm (not shown) similar to arm 330 on the other half of the anterior lens 322 not illustrated in FIG. 21. The posterior lens 324 includes optics 332 that are similar to the optics of posterior lens 124 discussed above. The posterior lens 324 also includes haptics 334. The haptics 334 include an arm 336, as shown. It is understood that the posterior lens 324 includes another arm (not shown) similar to arm 336 on the other half of the posterior lens 324 not illustrated in FIG. 21. The haptics 328, 334 and, in particular, the arms 330, 336 of the anterior and posterior lenses 322, 324 have properties that result in a desired offset (either distance or angle) of the optical axes of the optics 326, 332 of the anterior and posterior lenses. In that regard, the material properties of the haptics 328, 334, the geometrical structures of the haptics 328, 334, and/or combinations thereof are adjusted to achieve the desired offset. In some instances, a plurality of anterior lenses 322 and a plurality of posterior lenses 324 are provided in a kit to allow treating medical personnel to select the appropriate combination of the lenses to achieve a desired offset.

Generally, the lenses of the intra-ocular lens systems of the present disclosure may be formed of any suitable material. For example, in some instances the lenses are formed of a soft acrylic polymer (e.g., a material used to form commercially available lenses sold by Alcon under the trademark Acrysof®). In other embodiments, the lenses are formed of other suitable biocompatible materials, such as a silicone or hydrogel. In some instances, the haptics of the lenses are form of a different material than the optics. In such instances, the haptics may be formed of suitable polymeric materials, such as polymethylmethacrylate, polypropylene and the like. The lenses of the intra-ocular lens systems of the present disclosure may also be formed of the materials disclosed in U.S. Pat. No. 6,416,550, which is hereby incorporated by reference in its entirety. In some instances, the lenses are foldable to facilitate insertion using minimally invasive surgical techniques. In particular, the lenses may be configured to be inserted through an incision having a length less than 4.0 mm and, in some instances, less than 3.5 mm. In some embodiments, the lenses are configured for insertion using an intra-ocular lens cartridge system. Further, the lenses may be inserted separately or together. For example, in one embodiment the posterior lens is first inserted into the capsular bag and then the anterior lens is inserted into the capsular bag and engaged with the posterior lens.

The intra-ocular lens systems of the present disclosure are used in combination with other treatments in some instances. For example, when treating patients with AMD, any of the disclosed intra-ocular lens systems may be used in conjunction with administration of an AMD drug to stop and deter further development of AMD. In some instances, the AMD drug is an ophthalmic pharmaceutical preparation for the treatment of advanced macular degeneration. The AMD drug can steady and stabilize the vision to help the intra-ocular lens systems better improve the patient vision. Also, the intra-ocular lens systems are used with contact lenses, refractive ablations, and/or other treatments in some instances.

Further, while anterior surfaces of the posterior lenses have generally been illustrated as forming the negative optics of the posterior lens, this is for illustrative purposes of the operation principles of the devices and no limitation is intended thereby. Rather, it is understood that the anterior surface, the posterior surface, and/or combinations of the anterior and posterior surfaces of the posterior lens are utilized to form the negative optics in some embodiments. For example, in some instances the central portion of the anterior surface of the posterior lens is a positive optic and the central portion of the posterior surface is a negative optic. In other instances, central portions of both the anterior surface and the posterior surface are negative optics. In that regard, in some embodiments where central portions of both the anterior surface and the posterior surface are negative optics, the degree of the optics is decreased such that the total of effect of the negative optics of the anterior and posterior surfaces is substantially equal to the negative optics when only one of the surfaces is utilized.

While the embodiments described above focused on offsetting the optics of the anterior lens utilizing various methods (e.g., distance and angle), it is understood that no limitation is intended thereby. Generally, any means of producing a deflected, magnified image may be utilized. Further, it is understood that the same principles discussed with respect to the anterior lenses above may similarly be applied to offset the optics of the posterior lens. Accordingly, in some embodiments, the optics of the posterior lens are offset utilizing the features and methods described above. Further still, in some embodiments the optics of both the anterior and posterior lenses are offset utilizing the features and methods described above. Generally, the intra-ocular lens systems of the present disclosure may utilize any combination of offsets (e.g., distance and/or angle) in the optics of one or both of the anterior and posterior lenses.

Although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

What is claimed is:

1. An intra-ocular lens system, comprising:
   a first lens sized and shaped for implantation into a posterior chamber of an eye, the first lens having a positive power optic with a first optical axis; and
   a second lens sized and shaped for implantation into the posterior chamber of the eye and configured for engagement with the first lens, the second lens having an anterior surface and an opposing posterior surface, wherein a central portion of the second lens defines a negative surface power optic with a second optical axis and wherein a peripheral portion of the anterior surface defines a first positive surface power optic;

wherein:
the first lens and second lens are configured such that, upon implantation into the posterior chamber of an eye, they are mounted to one another in a fixed position to prevent motion of the first lens and the second lens relative to one another in response to any movement of a capsular bag of the posterior chamber of an eye; and the first optical axis and the second optical axis are spaced at a fixed distance and laterally and/or angularly offset with respect to one another when the first and second lenses are engaged to produce a magnified off-center image having an angular magnification of at least 1.5×.

2. The system of claim 1, wherein the central portion of the second lens defining the negative surface power optic includes a portion of the anterior surface.

3. The system of claim 2, wherein the central portion of the second lens defining the negative surface power optic includes a portion of the posterior surface.

4. The system of claim 2, wherein a central portion of the posterior surface has a second positive surface power optic and a peripheral portion of the posterior surface has a third positive surface power optic.

5. The system of claim 4, wherein the first and third positive surface power optics of the peripheral portions of the anterior and posterior surfaces of the second lens form a single focal optic with a power range between 6 diopters and 34 diopters.

6. The system of claim 5, wherein the positive power optic of the first lens has a first diameter and wherein the second lens has a second diameter greater than the first diameter such that, when the first and second lenses are engaged, light passing around the positive power optic of the first lens passes through the single focal optic formed by the peripheral portions of the anterior and posterior surfaces of the second lens.

7. The system of claim 2, wherein the angular magnification is between about 1.5× and about 4.0×.

8. The system of claim 7, wherein the positive power optic of the first lens and the negative surface power optic of the anterior surface of the second lens produce a substantially collimated light beam within the second lens that is projected onto a central portion of the posterior surface of the second lens having a second positive surface power optic.

9. The system of claim 1, wherein the first lens includes a first haptic system and the second lens includes a second haptic system, the first and second haptic systems configured to produce the offset between the first optical axis and the second optical axis.

10. The system of claim 9, wherein the first and second lenses are configured for implantation into the capsular bag, and wherein at least the first and second haptic systems are configured such that at least a portion of the first lens protrudes through a capsular rhexis after the capsular bag is shrink-wrapped around the first and second haptic systems.

11. The system of claim 9, wherein the first and second haptic systems are configured such that the positive power optic of the first lens is spaced from a central portion of the anterior surface of the second lens by a distance between about 2.0 mm and about 4.0 mm when the first and second lenses are engaged.

12. The system of claim 1, wherein the first and second lenses are foldable to facilitate implantation through an incision less than about 4.0 mm in length.

13. The system of claim 12, wherein the first and second lenses are configured for insertion utilizing a cartridge system.

14. The system of claim 1, wherein the central portion of the second lens defining the negative surface power optic includes a portion of the posterior surface.

15. The system of claim 1, wherein the first optical axis and the second optical axis extend substantially parallel to one another, but are offset by a distance between about 0.05 mm and about 0.75 mm.

16. The system of claim 1, wherein the first optical axis and the second optical axis are offset by an oblique angle between about 1 degree and about 15 degrees.

17. An apparatus comprising:
an anterior lens sized and shaped for implantation into a posterior chamber of an eye, the anterior lens defining a positive power optic having a first optical axis such that, in combination with a predicted optical power for a cornea of an eye based on patient measurement information, the anterior lens provides a back focal length between about 3.0 mm and about 5.0 mm; and a posterior lens sized and shaped for implantation into the posterior chamber of the eye in a position posterior to the anterior lens, the posterior lens having an anterior surface and an opposing posterior surface, wherein a central portion of the anterior surface defines a negative power optic surface having a second optical axis, wherein a peripheral portion of the anterior surface defines a first positive power optic surface, wherein a central portion of the posterior surface defines a second positive power optic surface, and wherein a peripheral portion of the posterior surface defines a third positive power optic surface, the first and third positive power optic surfaces of the peripheral portions of the anterior and posterior surfaces forming a single focal optic with a power range between 6 diopters and 34 diopters;

wherein the anterior and posterior lenses include haptics configured to space the anterior and posterior lenses by a fixed distance and to prevent the anterior and posterior lenses from moving relative to one another in response to any movement of a capsular bag of the posterior chamber of an eye and to laterally offset the first optical axis relative to the second optical axis by between about 0.05 mm and about 0.75 mm when the anterior and posterior lenses are implanted into the posterior chamber of the eye to produce a magnified off-center image, wherein the angular magnification is at least 1.5×.

18. The apparatus of claim 17, wherein the anterior and posterior lenses are configured for implantation into the capsular bag.

19. The apparatus of claim 18, wherein the haptics of the anterior and posterior lenses are configured such that at least a portion of the anterior lens protrudes through a capsular rhexis after the capsular bag is shrink-wrapped around the anterior and posterior lenses.

20. The apparatus of claim 17, wherein the haptics of the anterior and posterior lenses are configured such that the anterior lens is spaced from the posterior lens by a distance between about 2.0 mm and about 4.0 mm when the anterior and posterior lenses are implanted into the posterior chamber of the eye.

21. The apparatus of claim 20, wherein the anterior and posterior lenses are foldable to facilitate implantation through an incision less than about 4.0 mm in length.

22. The apparatus of claim 17, wherein the second and third positive power optic surfaces are surface portions of a single positive power optic surface.

* * * * *